United States Patent [19]

Tezuka et al.

[11] 4,278,657
[45] Jul. 14, 1981

[54] CREAMY OR MILKY SKIN COSMETIC COMPOSITIONS CONTAINING NATURAL MATERIALS AS EMULSIFYING AGENTS

[75] Inventors: Keizo Tezuka, Kaisei; Genichiro Okuyama, Odawara; Kazunobu Tokunaga, Odawara; Yasuhisa Otani, Odawara, all of Japan

[73] Assignee: Kanebo, Ltd., Tokyo, Japan

[21] Appl. No.: 52,263

[22] Filed: Jun. 26, 1979

[51] Int. Cl.³ .................... A61K 7/00; A61K 7/02; A61K 7/02
[52] U.S. Cl. .................... 424/63; 252/DIG. 5; 424/70; 424/358; 424/361; 424/362; 424/363; 424/364; 424/365
[58] Field of Search .................... 424/63, 70, 358–365; 252/DIG. 5

[56] References Cited

U.S. PATENT DOCUMENTS 3,746,012  7/1973  Deszyck .................... 131/140 P

FOREIGN PATENT DOCUMENTS 52-151736  12/1977  Japan .................... 424/358
1512083    5/1978   United Kingdom .................... 424/70

OTHER PUBLICATIONS

Murav'ev, (2) Chem Abs., vol. 68, 1968, Ab. No. 107868v.
Webster's Third New Int. Dict., G & C Merriam, pub., Springfield, MA, 1963, p. 2006.
Winter, A Consumer's Dict. of Cos. Ingredients, Crown Pub., NY, 1974, pp. 108–111, 158,159.
Murav'ev, Chem. Abs., vol. 82, 1975, Ab. No. 64385e.
Doi, Chem. Abs., vol. 75, 1971, Ab. No. 133025g.
Otsuka, Chem. Abs., vol. 84, 1976, Ab. No. 155579d.

Primary Examiner—Anna P. Fagelson

[57] ABSTRACT

Disclosed is a creamy or milky skin cosmetic composition consisting of an oil-in-water emulsion in which an oily substance is dispersed in water with the aid of an emulsifying agent composed of at least glycyrrhizic compound selected from glycyrrhizic acid and salts thereof and at least one water-soluble polysaccharide selected from pectin, karaya gum, locust bean gum and xanthan gum. This skin cosmetic composition causes no irritation to the skin and hence has great safety for the skin, as contrasted with skin cosmetic compositions containing synthetic emulsifiers. In addition, it exhibits very excellent emulsion stability and storage stability and presents a very attractive appearance (fine texture and good gloss) owing to the synergistic effect of the aforesaid glycyrrhizic compound and water-soluble polysaccharide.

8 Claims, 5 Drawing Figures

CREAMY OR MILKY SKIN COSMETIC COMPOSITIONS CONTAINING NATURAL MATERIALS AS EMULSIFYING AGENTS

BACKGROUND OF THE INVENTION (1) Field of the Invention

This invention relates to creamy or milky skin cosmetic compositions consisting of oil-in-water emulsions (hereinafter referred to as O/W emulsions) in which an oily substance is dispersed in water with the aid of an emulsifying agent composed of at least one naturally-occurring glycyrrhizic compound and at least one naturally-occurring water-soluble polysaccharide. More particularly, it relates to such skin cosmetic compositions which cause no irritation to the skin, have great safety and affinity for the skin, exhibit excellent storage stability and emulsion stability, and present an attractive appearance (fine texture and good gloss).

(2) Description of the Prior Art

It is well known in the prior art that skin cosmetics of the emulsion type, such as creams and milky lotions, are required to satisfy the following conditions:

(1) They must cause no irritation to the skin and hence have great safety for the skin.

(2) They must have good emulsion stability and storage stability.

(3) They must have good chemical stability including high resistance to hydrolysis.

(4) They must present an attractive appearance from the viewpoints of texture and gloss.

(5) They must have great affinity for the skin.

In order to meet these requirements, elaborate compositional designs are being made, for example, by selection of suitable emulsifying agents, search for useful combinations thereof, and concomitant use of special materials. However, it is not easy to accomplish this purpose. Specifically, it is very difficult to satisfy the above-described conditions by using a single emulsifying agent.

For example, nonionic surface active agents of the polyoxyethylene alkyl ether type are strongly irritative to the skin and poor in emulsifying power. Nonionic surface active agents of the ester type, such as (polyoxyethylene fatty acid esters, polyoxyethylene glycerol-fatty acid esters, polyoxyethylene sorbitan fatty acid esters and the like,) are poor in emulsifying power and resistance to hydrolysis.

Anionic surface active agent, such as sulfuric esters of higher alcohols, alkylarylsulfonic acid salts, and higher fatty acid salts and the like, have a strong degreasing power and cause irritation to the skin.

Cationic surface active agents and ampholytic surface active agents are also irritative to the skin.

On the other hand, dipotassium glycyrrhizinate and monoammonium glycyrrhizinate have only a weak emulsifying power. Thus, creams and milky lotions using these compounds alone are lacking in gloss and remarkably poor in storage stability, as will be described hereinafter.

Karaya gum, locust bean gum, xanthan gum and the like are characterized by thickening properties, but are poor in emulsifying power. Thus, they cannot provide any practical emulsion stability, as will be described later.

Pectin has a somewhat better emulsifying power than karaya gum, locust bean gum, xanthan gum and the like. Nevertheless, the use of pectin alone as emulsifying agent hardly produces emulsions having good emulsion stability and storage stability. U.S. Pat. No. 2,372,159 discloses cosmetic compositions in which an oily substance is dispersed in water by the combined use of a cationic surface active agent (cetyl trimethyl ammonium bromide) and pectin. However, these cosmetic compositions irritate the skin due to the cationic surface active agent.

In order to overcome the above-described difficulties with skin cosmetic compositions of the emulsion type, the present inventors have performed intensive and extensive studies and have discovered that, when an oily substance is dispersed in water by using a combination of a naturally-occurring glycyrrhizic compound and a specific water-soluble polysaccharide in place of a synthetic emulsifier, the synergistic effect of both natural materials brings about remarkable improvements in emulsifying power, emulsion stability, and emulsion homogeneity and thereby provides an O/W emulsion having excellent stability to long-term storage and temperature changes and presenting an attractive appearance (fine texture and good gloss) and, moreover, this emulsion exerts a mild action on the skin without causing irritation thereto and produces a variety of beneficial cosmetic effects. The present invention is based on this discovery.

SUMMARY OF THE INVENTION

It is an object of this invention to provide a creamy or milky skin cosmetic composition of the O/W emulsion type which exerts a mild action on the skin without causing irritation thereto, has great affinity for the skin, exhibits excellent storage stability and emulsion stability, and presents an attractive appearance (fine texture and good gloss).

It is another object of this invention to provide a novel emulsifying agent which is useful for such a purpose.

These and other objects of the invention are accomplished by a creamy or milky akin cosmetic composition of the oil-in-water (O/W) emulsion type which consists essentially of an emulsifying agent, an oily substance and water, the emulsifying agent being composed of at least one glycyrrhizic compound having the general formula where A, A' and A" independently represent hydrogen atoms, sodium atoms, potassium atoms, ammonium radicals or cationic radicals derived from alkanolamines, and at least one water-soluble polysaccharide selected from the group consisting of pectin, karaya gum, locust bean gum and xanthan gum.

BRIEF DESCRIPTION OF THE DRAWINGS

The magnification of the optical photomicrographs given in FIGS. 1 to 5 is 600 diameters.

DETAILED DESCRIPTION OF THE PREFERRED EMBODIMENTS

The glycyrrhizic compounds which are embraced by the general formula given above and can be used in the practice of the invention include glycyrrhizic acid and salts thereof such as monosodium glycyrrhizinate, monopotassium glycyrrhizinate, monoammonium glycyrrhizinate, monomonoethanolamine glycyrrhizinate, monodiethanolamine glycyrrhizinate, monotriethanolamine glycyrrhizinate, disodium glycyrrhizinate, dipotassium glycyrrhizinate, diammonium glycyrrhizinate, dimonoethanolamine glycyrrhyzinate, didiethanolamine glycyrrhizinate, ditriethanolamine glycyrrhizinate, trisodium glycyrrhizinate, tripotassium glycyrrhizinate, triammonium glycyrrhizinate, trimonoethanolamine glycyrrhizinate, tridiethanolamine glycyrrhizinate, and tritriethanolamine glycyrrhizinate. Among these compounds, glycyrrhizic acid, monosodium glycyrrhizinate, monopotassium glycyrrhizinate, monoammonium glycyrrhizinate, disodium glycyrrhizinate, dipotassium glycyrrhizinate, diammonium glycyrrhizinate, trisodium glycyrrhizinate, tripotassium glycyrrhizinate, and triammonium glycyrrhizinate are preferred. The foregoing glycyrrhizic compounds may be used alone or in combination.

The amount of glycyrrhizic compound used in the skin cosmetic composition of the invention is in the range of from 0.01 to 20.0% by weight, preferably from 0.1 to 3.0% by weight, and most preferably from 0.1 to 2.0% by weight, based on the total weight of the composition. If it is less than 0.01% by weight, its emulsifying power becomes so weak that the resulting skin cosmetic composition may fail to exhibit satisfactory emulsion stability and storage stability and to present an attractive appearance (fine texture and good gloss). If it is greater than 20% by weight, no additional benefits are gained and, moreover, the emulsifiability of the oily substance in water is apt to decrease.

Glycyrrhizic acid and salts thereof can be obtained in the following manner: Dried licorice roots are cut into small pieces and extracted with water in the cold. Ethanol is added to this aqueous extract and the resulting precipitate is filtered off. After addition of a mineral acid to the filtrate, the resulting precipitate was collected by filtration and washed with water to remove any residual mineral acid. The product thus obtained is glycyrrhizic acid. This glycyrrhizic acid is dissolved in an aqueous solution containing a base such as sodium hydroxide, potassium hydroxide, ammonia, monoethanolamine, diethanolamine or triethanolamine, and then evaporated to dryness. The residue is recrystallized from a solvent such as acetic acid or alcohol to obtain a monobasic salt of glycyrrhizic acid. Dibasic and tribasic salts of glycyrrhizic acid can also be obtained by dissolving the monobasic salt in the stoichiometric amount of the aforesaid aqueous solution containing a base and then evaporating it to dryness.

The water-soluble polysaccharides which can be used in the practice of the invention include pectin, karaya gum, locust bean gum and xanthan gum. Among them, pectin, karaya gum, xanthan gum, and mixture thereof are preferred. These water-soluble polysaccharides may be used alone or in combination.

The amount of water-soluble polysaccharide used in the skin cosmetic composition of the invention is in the range of from 0.1 to 10% by weight, preferably from 0.5 to 5% by weight, and most preferably from 0.5 to 3.5% by weight, based on the total weight of the composition. If it is less than 0.1% by weight, its emulsifying power is apt to become too weak. If it is greater than 10% by weight, its solubility and dispersibility in water are apt to decrease and the resulting skin cosmetic composition may fail to exhibit satisfactory storage stability and emulsion stability and to present an attractive appearance (fine texture and good gloss).

Preferably, pectin has a mean molecular weight of from 20,000 to 400,000 and a degree of methyl esterification of from 25 to 80%. The expression "degree of methyl esterification" as used herein means the percentage of methyl esterified carboxyl groups to all carboxyl groups of pectin.

The oily substances which can be used in the practice of the invention are well-known oily substances suitable for use in skin cosmetics and include, for example, higher aliphatic hydrocarbons such as liquid paraffin, squalane, vaseline, ceresin and the like; vegetable fats and oils such as olive oil, almond oil, avocado oil, castor oil, cacao butter, palm oil and the like; animal fats and oils such as cod liver oil, whale oil, beef tallow, butter fat and the like; waxes such as bees wax, carnauba wax, spermaceti, lanolin and the like; higher fatty acids such as lauric acid, myristic acid, palmitic acid, stearic acid, oleic acid, behenic acid, lanolin fatty acid and the like; higher alcohols such as lauryl alcohol, stearyl alcohol, cetyl alcohol, oleyl alcohol and the like; and straight-chain or branched-chain ester oils such as isopropyl myristate, butyl stearate, hexyl laurate, octyldodecyl myristate, diisopropyl adipate, diisopropyl sebacate, isocetyl myristate and the like. These oily substances may be used alone or in combination. The amount of oily substance used in the skin cosmetic composition of the invention is in the range of from 10 to 70% by weight and preferably from 15 to 60% by weight, based on the total weight of the composition.

The amount of water used in the skin cosmetic composition of the invention is in the range of from 30 to 90% by weight and preferably from 40 to 85% by weight, based on the total weight of the composition.

Where the skin cosmetic composition of the invention is adapted for use as a massage cream, cleansing cream, skin cream, skin milk, or the like, it is unnecessary to incorporate a pigment thereinto. However, where it is adapted for use as a foundation cream (under make-up cream) or liquid makeup base (under make-up milky lotion), a pigment is recommended to be incorporated thereinto in addition to the aforesaid ingredients. The amount of pigment used therein is in the range of not greater than 10% by weight and preferably from 0.5 to 7% by weight, based on the total weight of the composition. The pigments useful for this purpose include inorganic pigments such as titanium oxide, kaolin, yellow oxide of iron, red oxide of iron, black oxide of iron, talc and the like.

Furthermore, if desired, small amounts of cosmetically or pharmacologically effective substances, perfumes, antiseptics, and/or colorants may be added thereto.

The creamy or milky skin cosmetic composition of the invention can be prepared by any conventional procedure. For example, an aqueous solution is formed by dissolving at least one glycyrrhizic compound, at least one water-soluble polysaccharide, and an antiseptic in a predetermined amount of water at a temperature of from 70° to 85° C. While this aqueous solution is being stirred, an oily substance heated to a temperature of from 70° to 85° C. is added thereto and dispersed therein. The resulting emulsion is allowed to cool, during which a perfume is added thereto and mixed therein. (If it is desired to incorporate a pigment thereinto, the pigment is dispersed in the aforesaid aqueous solution before the oily substance is dispersed therein.)

The creamy or milky skin cosmetic composition of the invention consists essentially of an O/W emulsion in which an oily substance is dispersed in water with the aid of an emulsifying agent composed of at least one glycyrrhizic compound and at least one water-soluble polysaccharide. The droplets of oily substance present in the emulsion system are relatively fine and uniform, and protected and stabilized by both the glycyrrhizic compound and the water-soluble polysaccharide. For these reasons, the skin cosmetic composition of the invention presents an attractive and pleasing appearance characterized by a fine texture and a good gloss, and exhibits very excellent emulsion stability and storage stability.

These outstanding features is attributable to the synergistic effect of the glycyrrhizic compound and the water-soluble polysaccharide. This will become apparent from the results of comparison described in the succeeding Examples and Controls.

Since the glycyrrhizic compounds and water-soluble polysaccharides used in the practice of the invention exert a mild action on the skin without causing irritation thereto and hence have great safety for the skin, the skin cosmetic composition of the invention does not pose the problem of skin irritation as contracted with skin cosmetic compositions containing synthetic emulsifiers.

Furthermore, it is well known that glycyrrhizic acid and salts thereof are remarkably effective in the treatment of acute and chronic dermal diseases and are being used for external application in the field of dermatology. Thus, the skin cosmetic composition of the invention can be expected to have pharmacologically beneficial effects on the skin.

The skin cosmetic composition of the invention can be adapted for use as a massage cream, cleansing cream, skin cream, skin milk, cleansing milk, foundation cream, or liquid makeup base, whereby beneficial cosmetic effects will be produced.

SKIN IRRITATION TESTS ON GLYCYRRHIZIC COMPOUNDS AND WATER-SOLUBLE POLYSACCHARIDES (1) Preparation of Test Samples Aqueous solutions each containing pectin, karaya gum, locust gum, or xanthan gum at a concentration of 5% by weight, aqueous solutions each containing glycyrrhizic acid or one of its salts [compounds (1) to (18) listed in Table 1 of Example 2] at a concentration of 1% by weight, and aqueous solution each containing one of the aforesaid water-soluble polysaccharides at a concentration of 5% by weight and one of the aforesaid glycyrrhizic compounds at a concentration of 1% by weight were prepared and used as test samples.

For purposes of comparison, aqueous solutions each containing one of conventional synthetic emulsifiers (compounds No. 1 to No. 9 listed in the succeeding section (2) headed "Results of Skin Irritation Tests") at a concentration of 1% by weight were also prepared and used as test samples.

(2) Results of Skin Irritation Tests

Using the aforesaid test samples, animal skin irritation tests and human skin irritation tests were performed according to the procedure which will be described later. In the case of glycyrrhizic compounds and water-soluble polysaccharides, both the animal skin irritation score and the human skin irritation score were 0 for all test samples. In the case of conventional synthetic emulsifiers, however, the animal skin irritation score varied from 0.8 to 3.0 and the human skin irritation score varied from 2 to 14, as can be seen from the data given below. It is apparent, therefore, that the aforesaid glycyrrhizic compounds, water-soluble polysaccharides, and combinations thereof caused no irritation to the skin, but the conventional synthetic emulsifiers were irritative to the skin.

| Synthetic Emulsifier | Animal Skin Irritation Score | Human Skin Irritation Score |
|---|---|---|
| No. 1 Polyoxyethylene (10E.O) stearyl ether | 0.8 | 8 |
| No. 2 Polyoxyethylene (20E.O) sorbitan monostearate | 0.9 | 4 |
| No. 3 Polyoxyethylene (6E.O) sorbitan monooleate | 1.1 | 4 |
| No. 4 Polyoxyethylene (5E.O) glyceryl monostearate | 0.85 | 2 |
| No. 5 Sodium Lauryl sulfate | 2.0 | 10 |
| No. 6 Sodium cetyl sulfate | 1.8 | 8 |
| No. 7 Benzalkonium chloride | 3 | 14 |
| No. 8 Sodium N-lauloyl sarcosinate | 2.7 | 12 |
| No. 9 Cetyl trimethyl ammonium bromide | 2.6 | 14 |

(3) Animal Skin Irritation Tests
(i) Test Procedure

According to the Draize Technique, three albino rabbits weighing 2,500–3,500 gm were used. Hair on the back was clipped and 0.5 ml of the test sample was held in contact with the skin by means of a rubber sleeve.

The animals were immobilized in an animal holder with patches and the entire trunk of the animals was then wrapped with rubber cloth for 24 hours. After the 24 hours of exposure, the patches were removed, and the resulting reactions were evaluated on the criteria given below. Readings were made also after 72 hours and the final score represents an average of the 24 and 72 hour readings (ii) Evaluation of skin reactions

| (1) | Erythema and Eschar Formation | |
|---|---|---|
| | No erythema | 0 |
| | Very slight erythema | 1 |
| | Well defined erythema | 2 |
| | Moderate to severe Erythema | 3 |
| | Severe erythema to slight eschar | 4 |
| | (Total possible erythema score 4) | |
| (2) | Edema Formation | |
| | No edema | 0 |
| | Very slight edema | 1 |
| | Slight edema | 2 |
| | Moderate edema | 3 |
| | Severe edema | 4 |
| | (Total possible edema score 4) | |

(iii) Evaluation of irritant properties

An average score was evaluated on the following criteria.

| Less than 2 | only mildly irritation |
|---|---|
| From 2 to 5 | moderate irritation |
| Above 6 | severe irritation |

(4) Human Skin Irritation Tests
(i) Test Procedure

Randomly selected 25 male and 25 female subjects were employed. According to the closed patch test method, a test sample was applied to the inside of the upper arm or forearm and covered with a bandage. After 24 hours, the patches were removed and the reading of reaction was rated according to the criteria given below. Readings were made also after 48 hours.

(ii) Rating

| Negative reaction | (−) |
|---|---|
| Doubtful reaction: faint erythema | (−?) |
| Weak positive reaction | (+) |
| Strong positive reaction | (++) |
| Extreme positive reaction | (+++) |

(iii) Evaluation of patch-test reactions

The degree of irritation was evaluated on the basis of the percentage of positive cases rated as (+) or (++) or (+++). These animal skin irritation tests and human skin irritation tests revealed that pectin, karaya gum, locust bean gum, and xanthan gum as well as glycyrrhizic acid and salts thereof were not irritative to the skin.

This invention is further illustrated by the following examples. In these examples, all parts and percentages are by weight.

The gloss value was measured according to the method 2 described in JIS-Z8741-1962 (Methods for Gloss Measurement). The texture was evaluated by visual inspection. The storage stability was examined by placing a sample in a constant-temperature chamber having an internal temperature of 45° C., allowing it to stand for a predetermined period of time, and then observing the state of the emulsion system.

EXAMPLE 1 (MASSAGE CREAM)

A. Formulation

| (1) Bees wax | 2 | parts |
|---|---|---|
| (2) Liquid paraffin | 45 | parts |
| (3) Cetyl alcohol | 3 | parts |
| (4) Pectin* | 2.5 | parts |
| (5) Deionized water | 46.5 | parts |
| (6) Methylparaben (methyl p-hydroxybenzoate) | 0.2 | part |
| (7) Glycyrrhizic acid | 0.5 | part |
| (8) Perfume | 0.3 | part |

*This pectin had a mean molecular weight of 100,000 and a degree of methyl esterification of 65%.

B. Preparation and Evaluation

Pectin (4), methylparaben (6), and glycyrrhizic acid (7) were homogeneously dissolved in deionized water (5) at a temperature of 80° C. (solution 1). On the other hand, bees wax (1), liquid paraffin (2), and cetyl alcohol (3) were melted by heating them to 80° C. (solution 2). While the solution 1 was being stirred in a homomixer, the solution 2 was added thereto and dispersed therein. The resulting emulsion was allowed to cool and, as soon as a temperature of 70° C. was reached, a perfume (8) was added thereto. After its temperature dropped to 30°

C., the stirring was discontinued. The massage cream thus obtained was in the form of an O/W emulsion, and had a fine (good) texture and a good gloss (gloss value=82). It was found to be very stable after 4 months' storage in a constant-temperature chamber at 45° C.

COMPARATIVE EXAMPLE 1

The procedure of Example 1 was repeated except that the pectin was omitted and the amount of deionized water was increased to 49 parts. The resulting massage cream had a coarse texture and a poor gloss (gloss value=31). It separated into two layers after 4 hours storage in a constant-temperature chamber at 45° C., which indicates that it was poor in emulsion stability and storage stability.

COMPARATIVE EXAMPLE 2

The procedure of Example 1 was repeated except that the glycyrrhizic acid was omitted and the amount of deionized water was increased to 47.0 parts. The resulting massage cream separated into two layers after 2.5 months' storage in a constant-temperature chamber at 45° C., which indicates that it was poorer in storage stability than the massage cream of Example 1.

EXAMPLE 2

The procedure of Example 1 was repeated except that a variety of glycyrrhizic acid salts and other carboxylic acid salts (for comparative purposes) as listed in Table 1 were used as substitutes for the glycyrrhizic acid. The massage creams thus obtained were examined for texture, gloss, and storage stability at 45° C. The results are shown in Table 1.

EXAMPLE 3 (CLEANSING CREAM)

A. Formulation

| | | |
|---|---|---|
| (1) Liquid paraffin | 55 | parts |
| (2) Spermaceti | 2 | parts |
| (3) Octyldodecyl myristate | 5 | parts |
| (4) Cetyl alcohol | 3 | parts |
| (5) Karaya gum | 1.5 | parts |
| (6) Deionized water | 32.7 | parts |
| (7) Methylparabon | 0.2 | part |
| (8) Monoammonium glycyrrhizinate | 0.3 | part |
| (9) Perfume | 0.3 | part |

B. Preparation and Evaluation

Karaya gum (5), methylparaben (7), and monoammonium glycyrrhizinate (8) were homogeneously dissolved in deionized water (6) at a temperature of 80° C. (solution 1). On the other hand, liquid paraffin (1), spermaceti (2), octyldodecyl myristate (3), and cetyl alcohol (4) were melted by heating them to 80° C. (solution 2). While the solution 1 was being stirred in a homomixer, the solution 2 was added thereto and dispersed therein. The resulting emulsion was allowed to cool and, as soon as a temperature of 70° C. was reached, a perfume (9) was added thereto. After its temperature dropped to 30° C., the stirring was discontinued. The cleansing cream thus obtained was in the form of an O/W emulsion, and presented a very attractive appearance characterized by a very fine (very good) texture and a good gloss (gloss value=89). It was found to be very stable after 4 months' storage in a constant-temperature chamber at 45° C. In an organoleptic practical test, 44 out of 50 panelers reported that it had an excellent cleansing effect.

TABLE 1

| | Substitute Compound | Texture | Gloss Value | Storage Stability at 45° C. |
|---|---|---|---|---|
| 1. | Monosodium glycyrrhizinate | Very good | 85 | Stable after 4 months |
| 2. | Dosodium glycyrrhizinate | " | 83 | " |
| 3. | Monopotassium glycyrrhizinate | " | 87 | " |
| 4. | Dipotassium glycyrrhizinate | " | 80 | " |
| 5. | Monoammonium glycyrrhizinate | " | 90 | " |
| 6. | Diammonium glycyrrhizinate | " | 82 | " |
| 7. | Monomonoethanolamine glycyrrhizinate | Good | 75 | " |
| 8. | Monodiethanolamine glycyrrhizinate | " | 75 | " |
| 9. | Monotriethanolamine glycyrrhizinate | " | 78 | " |
| 10. | Ditriethanolamine glycyrrhizinate | " | 77 | " |
| 11. | Trisodium glycyrrhizinate | Very good | 80 | " |
| 12. | Triammonium glycyrrhizinate | " | 80 | " |
| 13. | Tridiethanolamine glycyrrhizinate | Good | 75 | " |
| 14. | Tripotassium glycyrrhizinate | Very good | 80 | " |
| 15. | Dimonoethanolamine glycyrrhizinate | Good | 76 | " |
| 16. | Didiethanolamine glycyrrhizinate | " | 74 | " |
| 17. | Trimonoethanolamine glycyrrhizinate | " | 75 | " |
| 18. | Tritriethanolamine glycyrrhizinate | " | 74 | " |
| 19. | Sodium pyrrolidonecarboxylate | Poor | 30 | Separated after a week |
| 20. | Sodium lactate | " | 35 | " |

It is evident from the data of Table 1 that the combined use of a glycyrrhizic compound as defined above and a water-soluble polysaccharide as defined above produces creamy skin cosmetic compositions (massage creams) having a fine texture, a good gloss, and excellent storage stability.

COMPARATIVE EXAMPLE 3

The procedure of Example 3 was repeated except that the karaya gum was omitted and the amount of deionized water was increased to 34.2 parts. The resulting cleansing cream separated into two layers 4 hours after preparation.

COMPARATIVE EXAMPLE 4

The procedure of Example 3 was repeated except that the monoammonium glycyrrhizinate was omitted and the amount of deionized water was increased to 33.0 parts. The resulting cleansing cream separated into two layers 3 hours after preparation.

EXAMPLE 4 (MASSAGE CREAM)

A. Formulation

| (1) Liquid paraffin | 50 | parts |
|---|---|---|
| (2) Karaya gum | 1.5 | parts |
| (3) Locust bean gum | 1.5 | parts |
| (4) Deionized water | 46.0 | parts |
| (5) Methylparaben | 0.2 | part |
| (6) Glycyrrhizic acid | 0.5 | part |
| (7) Perfume | 0.3 | part |

B. Preparation and Evaluation

A massage cream was prepared in substantially the same manner as described in Example 1. The resulting massage cream was in the form of an O/W emulsion, and presented an attractive appearance characterized by a fine (good) texture and a good gloss (gloss value=84). It was found to be very stable after 4 months' storage in a constant-temperature chamber at 45° C.

EXAMPLE 5 (SKIN CREAM)

A. Formulation

| (1) Squalane | 30 | parts |
|---|---|---|
| (2) Microcrystalline wax | 5 | parts |
| (3) Olive oil | 2 | parts |
| (4) Xanthan gum | 1 | part |
| (5) Deionized water | 61.2 | parts |
| (6) Methylparaben | 0.2 | part |
| (7) Monotriethanolamine glycyrrhizinate | 0.3 | part |
| (8) Perfume | 0.3 | part |

B. Preparation and Evaluation

Xanthan gum (4), methylparaben (6), and monotriethanolamine (7) were homogeneously dissolved or dispersed in deionized water (5) at a temperature of 80° C. (solution 1). On the other hand, squalane (1), microcrystalline wax (2), and olive oil (3) were melted by heating them to 80° C. (solution 2). While the solution 1 was being stirred in a homomixer, the solution 2 was added thereto and dispersed therein. The resulting emulsion was allowed to cool and, as soon as a temperature of 70° C. was reached, a perfume (8) was added thereto. After its temperature dropped to 30° C., the stirring was discontinued. The skin cream thus obtained was in the form of an O/W emulsion, and had a fine (good) texture and a good gloss (gloss value=81). It was found to be stable after 4 months' storage in a constant-temperature chamber at 45° C.

COMPARATIVE EXAMPLE 5

The procedure of Example 5 was repeated except that the xanthan gum was omitted and the amount of deionized water was increased to 62.2 parts. The resulting skin cream separated into two layers 5 hours after preparation.

COMPARATIVE EXAMPLE 6

The procedure of Example 5 was repeated except that the monotriethanolamine glycyrrhizinate was omitted and the amount of deionized water was increased to 61.5 parts. The resulting skin cream separated into two layers 20 days after preparation.

EXAMPLE 6 (SKIN CREAM)

A. Formulation (See Table 2.)

B. Preparation and Evaluation

Xanthan gum (4), karaya gum (5), monoammonium glycyrrhizinate (7), and methylparaben (8) were homogeneously dissolved in deionized water (6) at a temperature of 80° C. (solution 1). On the other hand, squalane (1), microcrystalline wax (2), and olive oil (3) were melted by heating them to 80° C. (solution 2). While the solution 1 was being stirred in a homomixer, the solution 2 was added thereto and dispersed therein. The resulting emulsion was allowed to cool and, as soon as a temperature of 70° C. was reached, a perfume (9) was added thereto. After its temperature dropped to 30° C., the stirring was discontinued.

TABLE 2

Figure 1:
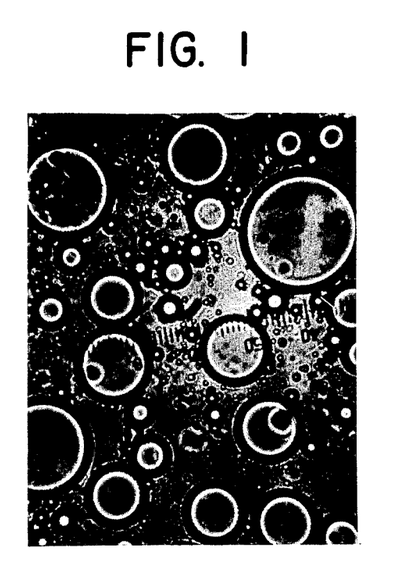
FIG. 1 is an optical photomicrograph showing the appearance (including size and uniformity) of oil droplets present in the emulsion system of a skin cream (No. 1 in Example 6) obtained by using monoammonium glycyrrhizinate as emulsifying agent.
Figure 2:
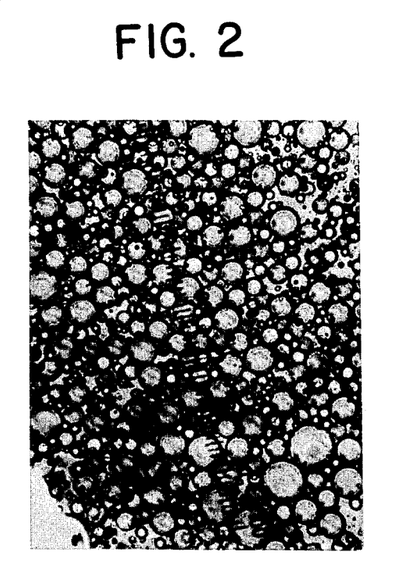
FIG. 2 is an optical photomicrograph showing the morphology of oil droplets present in the emulsion system of a skin cream (No. 2 in Example 6) obtained by using karaya gum as emulsifying agent.
Figure 3:
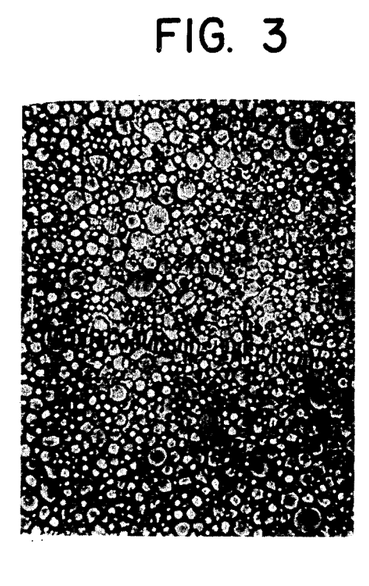
FIG. 3 is an optical photomicrograph showing the morphology of oil droplets present in the emulsion system of a skin cream (No. 3 in Example 6) obtained by using karaya gum and monoammonium glycyrrhizinate as emulsifying agents.
Figure 4:
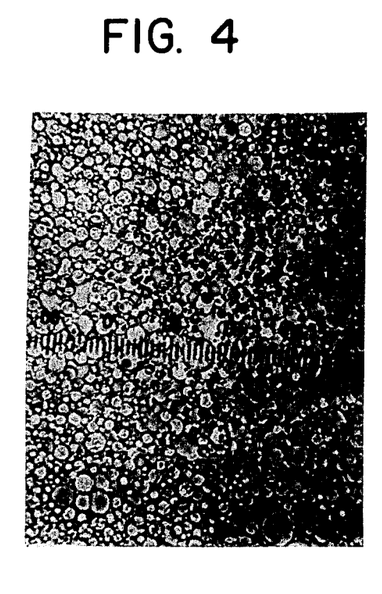
FIG. 4 is an optical photomicrograph showing the morphology of oil droplets present in the emulsion system of a skin cream (No. 4 in Example 6) obtained by using xanthan gum and monoammonium glycyrrhizinate as emulsifying agents.
Figure 5:
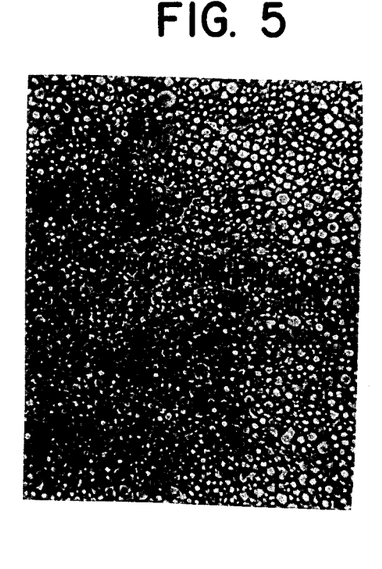
FIG. 5 is an optical photomicrograph showing the morphology of oil droplets present in the emulsion system of a skin cream (No. 5 in Example 6) obtained by using xanthan gum, karaya gum, and monoammonium glycyrrhizinate as emulsifying agents.

| | Skin Cream | | | | |
|---|---|---|---|---|---|
| Ingredient | No. 1** (parts) | No. 2** (parts) | No. 3* (parts) | No. 4* (parts) | No. 5* (parts) |
| 1. Squalane | 30 | 30 | 30 | 30 | 30 |
| 2. Microcrystalline wax | 5 | 5 | 5 | 5 | 5 |
| 3. Olive oil | 2 | 2 | 2 | 2 | 2 |
| 4. Xanthan gum | — | — | — | 0.7 | 0.7 |
| 5. Karaya gum | — | 1.5 | 1.5 | — | 1.5 |
| 6. Deionized water | 62.3 | 61.1 | 60.8 | 61.6 | 60.1 |
| 7. Monoammonium glycyrrhizinate | 0.3 | — | 0.3 | 0.3 | 0.3 |
| 8. Methylparaben | 0.2 | 0.2 | 0.2 | 0.2 | 0.2 |
| 9. Perfume | 0.2 | 0.2 | 0.2 | 0.2 | 0.2 |
| Optical Photomicrograph | FIG. 1 | FIG. 2 | FIG. 3 | FIG. 4 | FIG. 5 |
| Storage Stability at 45° C. | Separated after 4 hours | Seperated after 20 days | Stable after 4 months | Stable after 4 months | Stable after 4 months |
| Gloss Value | 31 (poor) | 41 (poor) | 81 (Very good) | 84 (Very good) | 90 (Very good) |
| Texture | Poor | Poor | | Very good | |

TABLE 2-continued

|  | Skin Cream | | | | |
|---|---|---|---|---|---|
| Ingredient | No. 1** (parts) | No. 2** (parts) | No. 3* (parts) | No. 4* (parts) | No. 5* (parts) |
|  | (coarse) | (coarse) |  | (very fine) |  |

*These skin creams are within the scope of this invention.
**These skin creams are outside the scope of this invention and are listed for purposes of comparison.

It is evident from the data of Table 2 that the use of a glycyrrhizic compound alone or a water-soluble polysaccharide alone produces skin creams poor in storage stability and appearance (texture and gloss), but their combined use produces skin creams having excellent storage stability and presenting an attractive appearance characterized by a fine texture and a good gloss.

EXAMPLE 7 (CLEANSING MILK)

A. Formulation

| (1) Liquid paraffin | 29 | parts |
|---|---|---|
| (2) Cetyl alcohol | 1 | part |
| (3) Pectin* | 2.5 | parts |
| (4) Deionized water | 66.7 | parts |
| (5) Methylparaben | 0.2 | part |
| (6) Dipotassium glycyrrhizinate | 0.3 | part |
| (7) Perfume | 0.3 | part |

*This pectin had a mean molecular weight of 150,000 and a degree of methyl esterification of 35%.

B. Preparation and Evaluation

Pectin (3), methylparaben (5), and dipotassium glycyrrhizinate (6) were homogeneously dissolved in deionized water (4) at a temperature of 80° C. (solution 1). On the other hand, liquid paraffin (1) and cetyl alcohol (2) were melted by heating them to 80° C. (solution 2). While the solution 1 was being stirred in a homomixer, the solution 2 was added thereto and dispersed therein. The resulting emulsion was allowed to cool and, as soon as a temperature of 70° C. was reached, a perfume (7) was added thereto. After its temperature dropped to 30° C., the stirring was discontinued. The cleansing milk thus obtained was in the form of an O/W emulsion having a viscosity of 6,000 cps, and presented an attractive appearance characterized by a fine (good) texture and a good gloss (gloss value=82). It was found to be very stable after 4 months' storage in a constant-temperature chamber at 45° C.

COMPARATIVE EXAMPLE 7

The procedure of Example 7 was repeated except that the dipotassium glycyrrhizinate was omitted and the amount of deionized water was increased to 67.0 parts. The resulting cleansing milk separated into two layers after 2.5 months'0 storage in a constant-temperature chamber at 45° C.

COMPARATIVE EXAMPLE 8

The procedure of Example 7 was repeated except that the pectin was omitted and the amount of deionized water was increased to 69.2 parts. The resulting cleansing milk separated into two layers 5 hours after preparation.

EXAMPLE 8 (SKIN MILK)

A. Formulation

| (1) Squalane | 15 | parts |
|---|---|---|

-continued

| (2) Cetyl alcohol | 0.5 | part |
|---|---|---|
| (3) Isocetyl myristate | 5 | parts |
| (4) Spermaceti | 1 | part |
| (5) Locust bean gum* | 1.5 | parts |
| (6) Deionized water | 76.2 | parts |
| (7) Methylparaben | 0.2 | part |
| (8) Monoammonium glycyrrhizinate | 0.3 | part |
| (9) perfume | 0.3 | part |

*This locust bean gum had a mean molecular weight of 300,000.

B. Preparation and Evaluation

Locust bean gum (5), methylparaben (7), and monoammonium glycyrrhizinate (8) were homogeneously dissolved in deionized water (6) at a temperature of 80° C. (solution 1). On the other hand, squalane (1), cetyl alcohol (2), isocetyl myristate (3), and spermaceti (4) were melted by heating them to 80° C. (solution 2). While the solution 1 was being stirred in a homomixer, the solution 2 was added thereto and dispersed therein. The resulting emulsion was allowed to cool and, as soon as a temperature of 70° C. was reached, a perfume (9) was added thereto. After its temperature dropped to 30° C., the stirring was discontinued. The skin milk thus obtained was in the form of an O/W emulsion having a viscosity of 7,200 cps, and presented an attractive appearance characterized by a fine (good) texture and a good gloss (gloss value=85). It was found to be very stable after 4 months' storage in a constant-temperature chamber at 45° C.

COMPARATIVE EXAMPLE 9

The procedure of Example 8 was repeated except that the monoammonium glycyrrhizinate was omitted and the amount of deionized water was increased to 76.5 parts. The resulting skin milk separated into two layers 4 hours after preparation.

COMPARATIVE EXAMPLE 10

The procedure of Example 8 was repeated except that the locust bean gum was omitted and the amount for deionized water was increased to 77.7 parts. The resulting skin milk separated into two layers 7 hours after preparation.

EXAMPLE 9 (FOUNDATION CREAM)

A. Formulation

| (1) Liquid paraffin | 45 | parts |
|---|---|---|
| (2) Xanthan gum | 0.7 | part |
| (3) Pectin | 0.5 | part |
| (4) Deionized water | 49.76 | parts |
| (5) Titanium dioxide | 1.5 | parts |
| (6) Kaolin | 1.5 | parts |
| (7) Red oxide of iron | 0.02 | part |
| (8) Yellow oxide of iron | 0.02 | part |
| (9) Methylparaben | 0.2 | part |
| (10) Glycyrrhizic acid | 0.5 | part |
| (11) Perfume | 0.3 | part |

B. Preparation and Evaluation

Xanthan gum (2), pectin (3), titanium dioxide (5), kaolin (6), red oxide of iron (7), yellow oxide of iron (8), methylparaben (9), and glycyrrhizic acid (10) were homogeneously dissolved or dispersed in deionized water (4) at a temperature of 80° C. (solution 1). On the other hand, liquid paraffin (1) was heated to 80° C. (solution 2). While the solution 1 was being stirred in a homomixer, the solution 2 was added thereto and dispersed therein. The resulting emulsion was allowed to cool and, as soon as a temperature of 70° C. was reached, a perfume (11) was added thereto. After its temperature dropped to 30° C., the stirring was discontinued. The foundation cream thus obtained was in the form of an O/W emulsion, and presented an attractive appearance characterized by a fine (good) texture and a good gloss. It was found to be very stable after 4 months' storage in a constant-temperature chamber at 45° C.

COMPARATIVE EXAMPLE 11

The procedure of Example 9 was repeated except that the pectin and the xanthan gum were omitted and the amount of deionized water was increased to 50.96 parts. The resulting foundation cream separated into two layers 6 hours after preparation.

COMPARATIVE EXAMPLE 12

The procedure of Example 9 was repeated except that the glycyrrhizic acid was omitted and the amount of deionized water was increased to 50.26 parts. The resulting foundation cream separated into two layers after 2.5 months' storage in a constant-temperature chamber at 45° C.

COMPARATIVE EXAMPLE 13

The procedure of Example 4 was repeated except that the glycyrrhizic acid was omitted and the amount of deionized water was increased to 46.5 parts. The resulting massage cream separated into two layers 3 hours after preparation.

COMPARATIVE EXAMPLE 14

The procedure of Example 4 was repeated except that the locust bean gum and the karaya gum were omitted and the amount of deionized water was increased to 49.0 parts. The resulting massage cream separated into two layers 5 hours after preparation.

EXAMPLE 10 (Skin Cream)

A. Formulation

| | | |
|---|---|---|
| (1) Squalane | 30 | parts |
| (2) Microcrystalline wax | 5 | parts |
| (3) Olive oil | 2 | parts |
| (4) Pectin* | 1 | part |
| (5) Karaya gum** | 1 | part |
| (6) Deionized water | 60.2 | parts |
| (7) Dipotassium glycyrrhizinate | 0.3 | part |
| (8) Methylparaben | 0.2 | part |
| (9) Perfume | 0.3 | part |

*This pectin had a mean molecular weight of 250,000 and a degree of methyl esterification of 60%.
**This karaya gum had a mean molecular weight of 150,000.

B. Preparation and Evaluation

A skin cream was prepared in substantially the same manner as described in Example 6. The resulting skin cream was in the form of an O/W emulsion, and presented a very attractive appearance characterized by a very fine (very good) texture and a very good gloss (gloss value=91). It was found to be stable after 4 months' storage in a constant-temperature chamber at 45° C.

COMPARATIVE EXAMPLE 15

The procedure of Example 10 was repeated except that the dipotassium glycyrrhizinate was omitted and the amount of deionized water was increased to 60.5 parts. The resulting skin cream separated into two layers after 2.5 months' storage in a constant-temperature chamber at 45° C.

COMPARATIVE EXAMPLE 16

The procedure of Example 10 was repeated except that the pectin and the karaya gum were omitted and the amount of deionized water was increased to 62.2 parts. The resulting skin cream separated into two layers 6 hours after preparation.

EXAMPLE 11 (Skin Milk)

A. Formulation

| | | |
|---|---|---|
| (1) Squalane | 15 | parts |
| (2) Olive oil | 3 | parts |
| (3) Octyldodecyl myristate | 3 | parts |
| (4) Spermaceti | 1 | part |
| (5) Locust bean gum* | 1.5 | parts |
| (6) Deionized water | 75.75 | parts |
| (7) Methylparaben | 0.2 | part |
| (8) Monoammonium glycyrrhizinate | 0.1 | part |
| (9) Dipotassium glycyrrhizinate | 0.15 | part |
| (10) Perfume | 0.3 | part |

*This locust bean gum had a mean molecular weight of 250,000.

B. Preparation and Evaluation

A skin milk was prepared in substantially the same manner as described in Example 8. The resulting skin milk was in the form of an O/W emulsion having a viscosity of 6,100 cps, and presented an attractive appearance characterized by a fine (good) texture and a good gloss (gloss value=82). It was found to be stable after 4 months' storage in a constant-temperature chamber at 45° C.

COMPARATIVE EXAMPLE 17

The procedure of Example 11 was repeated except that the locust bean gum was omitted and the amount of deionized water was increased to 77.25 parts. The resulting skin milk separated into two layers 5 hours after preparation.

COMPARATIVE EXAMPLE 18

The procedure of Example 11 was repeated except that the monoammonium glycyrrhizinate and the dipotassium glycyrrhizinate were omitted and the amount of deionized water was increased to 76.0 parts. The resulting skin milk separated into two layers 2 hours after preparation.

EXAMPLE 12 (Skin Milk)

The procedure of Example 11 was repeated except that 1.5 parts of xanthan gum was used as a substitute for the locust bean gum. The resulting skin milk was in the form of an O/W emulsion having a viscosity of 6,300 cps, and presented a very attractive appearance characterized by a very fine (very good) texture and a very good gloss (gloss value=89). It was found to be stable after 4 months' storage in a constant-temperature chamber at 45° C.

COMPARATIVE EXAMPLE 19

The procedure of Example 11 was repeated except that 1.5 parts of xanthan gum was used as a substitute for the locust bean gum and the monoammonium glycyrrhizinate and the dipotassium glycyrrhizinate were omitted. The resulting skin milk separated into two layers 3 hours after preparation.

EXAMPLE 13 (Liquid Makeup Base)

A. Formulation

| (1) | Liquid paraffin | 20 | parts |
|---|---|---|---|
| (2) | Olive oil | 5 | parts |
| (3) | Pectin* | 2 | parts |
| (4) | Deionized water | 70.66 | parts |
| (5) | Monoammonium glycyrrhizinate | 0.3 | part |
| (6) | Titanium oxide | 1.5 | parts |
| (7) | Ferric oxide | 0.02 | part |
| (8) | Yellow iron oxide | 0.02 | part |
| (9) | Methylparaben | 0.2 | part |
| (10) | Perfume | 0.3 | part |

*This pectin had a mean molecular weight of 300,000 and a degree of methyl esterification of 75%.

B. Preparation and Evaluation

Pectin (3), monoammonium glycyrrhizinate (5), titanium oxide (6), ferric oxide (7), yellow iron oxide (8), and methylparaben (9) were homogeneously dissolved or dispersed in deionized water (4) at a temperature of 80° C. (solution 1). On the other hand, liquid paraffin (1) and olive oil (2) were mixed and heated to 80° C. (solution 2). While the solution 1 was being stirred in a homomixer, the solution 2 was added thereto and dispersed therein. The resulting emulsion was allowed to cool and, as soon as a temperature of 70° C. was reached, a perfume (10) was added thereto. After its temperature dropped to 30° C., the stirring was discontinued. The liquid makeup base thus obtained was in the form of an O/W emulsion, and presented a very attractive appearance characterized by a fine (good) texture and a good gloss (gloss value=84). It was found to be stable after 4 months' storage in a constant-temperature chamber at 45° C.

COMPARATIVE EXAMPLE 20

The procedure of Example 13 was repeated except that the pectin was omitted and the amount of deionized water was increased to 72.66 parts. The resulting liquid makeup base separated into two layers 5 hours after preparation.

COMPARATIVE EXAMPLE 21

The procedure of Example 13 was repeated except that the monoammonium glycyrrhizinate was omitted and the amount of deionized water was increased to 70.96 parts. The resulting liquid makeup base separated into two layers after 2.5 months' storage in a constant-temperature chamber at 45° C.

EXAMPLE 14 (Cleansing Creams)

A. Formulation (See Table 3.)

TABLE 3

| Ingredient | No. 1** (parts) | No. 2* (parts) | No. 3* (parts) | No. 4* (parts) | No. 5* (parts) | No. 6* (parts) | No. 7* (parts) |
|---|---|---|---|---|---|---|---|
| 1. Liquid paraffin | 45 | 45 | 45 | 45 | 45 | 45 | 45 |
| 2. Octyldodecyl myristate | 5 | 5 | 5 | 5 | 5 | 5 | 5 |
| 3. Karaya gum | 0 | 0.1 | 0.5 | 3.5 | 5 | 10 | 15 |
| 4. Deionized water | 49.2 | 49.1 | 48.7 | 45.7 | 44.2 | 39.2 | 34.2 |
| 5. Methylparaben | 0.2 | 0.2 | 0.2 | 0.2 | 0.2 | 0.2 | 0.2 |
| 6. Monoammonium glycyrrhizinate | 0.3 | 0.3 | 0.3 | 0.3 | 0.3 | 0.3 | 0.3 |
| 7. Perfume | 0.3 | 0.3 | 0.3 | 0.3 | 0.3 | 0.3 | 0.3 |

| Ingredient | No. 8** (parts) | No. 9* (parts) | No. 10* (parts) | No. 11* (parts) | No. 12* (parts) | No. 13* (parts) | No. 14* (parts) |
|---|---|---|---|---|---|---|---|
| 1. Liquid paraffin | 45 | 45 | 45 | 45 | 45 | 45 | 45 |
| 2. Octyldodecyl myristate | 5 | 5 | 5 | 5 | 5 | 5 | 5 |
| 3. Karaya gum | 1.5 | 1.5 | 1.5 | 1.5 | 1.5 | 1.5 | 1.5 |
| 4. Deionized water | 48 | 47.99 | 47.9 | 46 | 45 | 38 | 33 |
| 5. Methylparaben | 0.2 | 0.2 | 0.2 | 0.2 | 0.2 | 0.2 | 0.2 |
| 6. Monoammonium glycyrrhizinate | 0 | 0.01 | 0.1 | 2.0 | 3.0 | 10 | 15 |
| 7. Perfume | 0.3 | 0.3 | 0.3 | 0.3 | 0.3 | 0.3 | 0.3 |

*These cleansing creams are within the scope of this invention.
**These cleansing creams are outside the scope of this invention and are listed for purposes of comparison.

B. Preparation and Evaluation

Cleansing creams were prepared in substantially the same manner as described in Example 3. The appearance (texture and gloss) and stability of the resulting cleansing creams are shown in Table 4.

TABLE 4

| Cleansing Cream | Texture | Gloss Value | Storage Stability at 45° C. |
|---|---|---|---|
| No. 1 | Poor (very coarse) | — | Separated 4 hours after preparation |
| No. 2 | Good (fine) | 72 (good) | Stable after 4 months |
| No. 3 | Very good (very fine) | 87 (very good) | " |
| No. 4 | Very good (very fine) | 90 (very good) | " |
| No. 5 | Very good (very fine) | 80 (very good) | " |
| No. 6 | Good (fine) | 70 (good) | " |
| No. 7 | Poor (coarse) | 39 (poor) | Separated 25 hours after preparation |
| No. 8 | Poor (very coarse) | 30 (poor) | Separated 5 hours after preparation |
| No. 9 | Good (fine) | 74 (good) | Stable after 4 months |

TABLE 4-continued

| Cleansing Cream | Texture | Gloss Value | Storage Stability at 45° C. |
|---|---|---|---|
| No. 10 | Very good (very fine) | 87 (very good) | " |
| No. 11 | Very good (very fine) | 90 (very good) | " |
| No. 12 | Very good (very fine) | 84 (very good) | " |
| No. 13 | Good (fine) | 72 (good) | " |
| No. 14 | Poor (coarse) | 31 (poor) | Separated 26 hours after preparation |

It is evident from the data of Table 4 that the amount of glycyrrhizic compound used in the skin cosmetic composition of the invention may be from 0.01 to 20% by weight, preferably from 0.1 to 3% by weight, and most preferably from 0.1 to 2% by weight, based on the total weight of the composition. Similarly, the amount of water-soluble polysaccharide used therein may be from 0.1 to 10% by weight, preferably from 0.5 to 5% by weight, and most preferably from 0.5 to 3.5% by weight, based on the total weight of the composition.

What is claimed is:

1. A creamy or milky skin cosmetic composition of the oil-in-water emulsion type which consists essentially of an emulsifying agent, an oily substance and water, said oily substance consisting of from 10 to 70% by weight based on the composition and selected from the group consisting of higher aliphatic hydrocarbons, vegetable fats and oils, animal fats and oils, waxes, higher alcohols, higher fatty acids and ester oils, said water constituting from 30 to 90% by weight of the composition, and said emulsifying agent being composed of at least one naturally-occurring glycyrrhizic compound in amounts of from 0.01 to 20.0% by weight based on the composition and having the general formula where A, A' and A" independently represent hydrogen atoms, sodium atoms, potassium atoms, ammonium radicals or cationic radicals derived from alkanol-amines and at least one water-soluble polysaccharide in amounts of from 0.1 to 10.0% by weight based on the composition and selected from the group consisting of pectin, karaya gum, locust bean gum and xanthan gum.

2. The skin cosmetic composition of claim 1 wherein the glycyrrhizic compound is at least one compound selected from the group consisting of glycyrrhizic acid, monosodium glycyrrhizinate, monopotassium glycyrrhizinate, monoammonium glycyrrhizinate, monomonoethanolamine, glycyrrhizinate, monodiethanolamine glycyrrhizinate, monotriethanolamine glycyrrhizinate, disodium glycyrrhizinate, dipotassium glycyrrhizinate, diammonium glycyrrhizinate, dimonoethanolamine glycyrrhizinate, didiethanolamine, glycyrrhizinate, ditriethanolamine glycyrrhizinate, trisodium glycyrrhizinate, tripotassium glycyrrhizinate, triammonium glycyrrhizinate, trimonoethanolamine glycyrrhizinate, tridiethanolamine glycyrrhizinate and tritriethanolamine glycyrrhizinate.

3. The skin cosmetic composition of claim 1 wherein the glycyrrhizic compound is at least one compound selected from the group consisting of glycyrrhizic acid, monosodium glycyrrhizinate, monopotassium glycyrrhizinate, monoammonium glycyrrhizinate, disodium glycyrrhizinate, dipotassium glycyrrhizinate, diammonium glycyrrhizinate, trisodium glycyrrhizinate, tripotassium glycyrrhizinate and triammonium glycyrrhizinate.

4. The skin cosmetic composition of claim 1 wherein the pectin has a mean molecular weight of from 20,000 to 400,000 and a degree of methyl esterification of from 25 to 80%.

5. The skin cosmetic composition of claim 1 which is adapted for use as a massage cream, cleansing cream, skin cream, skin milk or cleansing milk.

6. The skin cosmetic composition of claim 1 wherein a pigment is additionally present in an amount of not greater than 10% by weight based on the total weight of the composition.

7. The skin cosmetic composition of claim 6 wherein the pigment is at least one inorganic pigment selected from the group consisting of titanium dioxide, kaolin, yellow oxide of iron, red oxide of iron, black oxide of iron and talc.

8. The skin cosmetic composition of claim 7 which is adapted for use as a foundation cream or liquid makeup base.

* * * * *